(12) United States Patent
Mestha et al.

(10) Patent No.: US 8,768,438 B2
(45) Date of Patent: Jul. 1, 2014

(54) DETERMINING CARDIAC ARRHYTHMIA FROM A VIDEO OF A SUBJECT BEING MONITORED FOR CARDIAC FUNCTION

(75) Inventors: Lalit Keshav Mestha, Fairport, NY (US); Beilei Xu, Penfield, NY (US); Paul R. Austin, Webster, NY (US)

(73) Assignee: Xerox Corporation, Norwalk, CT (US)

(*) Notice: Subject to any disclaimer, the term of this patent is extended or adjusted under 35 U.S.C. 154(b) by 55 days.

(21) Appl. No.: 13/532,128

(22) Filed: Jun. 25, 2012

(65) Prior Publication Data

US 2013/0345569 A1    Dec. 26, 2013

(51) Int. Cl.
*A61B 6/00* (2006.01)

(52) U.S. Cl.
USPC .......................................................... 600/473

(58) Field of Classification Search
USPC .......................................................... 600/473
See application file for complete search history.

(56) References Cited

U.S. PATENT DOCUMENTS

| | | | |
|---|---|---|---|
| 7,336,982 B2 | 2/2008 | Yoo | |
| 2007/0021673 A1* | 1/2007 | Arbel et al. | 600/500 |
| 2009/0102966 A1* | 4/2009 | Jiang et al. | 348/448 |
| 2009/0326349 A1* | 12/2009 | McGonigle et al. | 600/323 |
| 2011/0251493 A1 | 10/2011 | Poh et al. | |

OTHER PUBLICATIONS

Sun et al., Motion-compensated noncontact imaging photoplethysmography to monitor cardiorespiratory status during exercise, Journal of Biomedical Optics 16:7, 077010, Jul. 2011.*
Selvaraj et al., Assessment of heart rate variability derived from finger-tip photoplethysmography as compared to electrocardiography, Journal of Medical Engineering & Technology, vol. 32, No. 6, Nov./Dec. 2008, 479-484.*
Olsson et al., Photoplethysmography for simultaneous recording of heart and respiratory rates in newborn infants, Acta Paediatr. Jul. 2000;89(7):853-61.*
Wei Lu et al., "Approach and Applications of Constrained ICA", IEEE Transactions on Neural Networks, vol. 16, No. 1, Jan. 2005.
Wei Lu et al., "Constrained Independent Component Analysis", School of Computer Engineering, Nanyang Technological University, Singapore 639798.
Takano et al., "Heart rate measurement based on a time-lapse image", Medical Engineering & Physics 29 (2007), pp. 853-857, www.sciencedirect.com.

(Continued)

*Primary Examiner* — Long V. Le
*Assistant Examiner* — Bo J Peng
(74) *Attorney, Agent, or Firm* — Philip E. Blair; Fleit Gibbons Gutman Bongini & Bianco P.L.

(57) ABSTRACT

What is disclosed is a system and method for processing a time-series signal generated by video images captured of a subject of interest in a non-contact, remote sensing environment such that the existence of a cardiac arrhythmia can be determined for that subject. In one embodiment, a time-series signal generated is received. The time-series signal was generated from video images captured of a region of exposed skin where photoplethysmographic (PPG) signals of a subject of interest can be registered. Signal separation is performed on the time-series signal to extract a photoplethysmographic signal for the subject. Peak-to-peak pulse points are detected in the PPG signal using an adaptive threshold technique with successive thresholds being based on variations detected in previous magnitudes of the pulse peaks. The pulse points are then analyzed to obtain peak-to-peak pulse dynamics. The existence of cardiac arrhythmias is determined for the subject based on the pulse dynamics.

21 Claims, 9 Drawing Sheets

(56) References Cited

OTHER PUBLICATIONS

Poh et al., "Non-contact, automated cardiac pulse measurements using video imaging and blind source separation.", May 10, 2010, vol. 18, No. 10/Optics Express 10762.
Lee et al., "Temporally constrained ICA-based foetal ECG separation", Electronics Letters, Oct. 13, 2005, vol. 41, No. 21.
Mestha et al., "Systems and Methods for Non-Contact Heart Rate Sensing", U.S. Appl. No. 13/247,575, filed Sep. 28, 2011.
Xu et al., "A Multi-Layer Array for a Multi-Resolution Multi-Spectral Camera," U.S. Appl. No. 13/239,642 filed Sep. 22, 2011.
Yang et al., "Vital Sign Estimation from Passive Thermal Video," IEEE Conference on Computer Vision and Pattern Recognition, Jun. 2008, pp. 23-28.
Garbey et al., "Contact-Free Measurement of Cardiac Pulse Based on the Analysis of Thermal Imagery," IEEE Transactions on Biomedical Engineering, Aug. 2007, vol. 54, No. 8, pp. 2-13.
Mestha et al., "Method for Classifying a Pixel of a Hyperspectral Image in a Remote Sensing Application," U.S. Appl. No. 13/023,310, filed Feb. 8, 2011.
Wang et al., "Determining a Total Number of People in a IR Image Obtained Via an IR Imaging System," U.S. Appl. No. 12/967,775, filed Dec. 14, 2010.
Xu et al., "System and Method for Object Identification and Tracking," U.S. Appl. No. 13/247,343, filed Sep. 28, 2011.
Lee et al., "Speech Coding Noise Reduction Using Ice-Based Speech Features," in P. Pajunen and J. Karhunen (eds.), Proc. Second International Workshop on Independent Component and Analysis and Blind Signal Separation, 2000.
Hoyer et al., "ICA Features of Colour and Stereo Images," P. Pajunen and J. Karhunen (eds.), Proc. Second International Workshop on Independent Component and Analysis and Blind Signal Separation, 2000, pp. 567-572.
Bell et al., The "Independent Components" of Natural Science are Edge Filters," Vision Ref., 1997, vol. 37, No. 23, pp. 3327-3338.
Lee et al., "Application of independent component analysis to microarrays," Genome Biology, 2003, vol. 4, Issue 11, R76.
Cantelli, Mark, "Are you in There?" TOLLTRANS 2011, www.TrafficTechnologyToday.com.
Mestha, et al., "Estimating Cardiac Pulse Recovery From Multi-Channel Source Data Via Constrained Source Separation", U.S. Appl. No. 13/247,683, filed Sep. 28, 2011.
Mestha et al., "Filtering Source Video Data Via Independent Component Selection", U.S. Appl. No. 13/281,975, filed Nov. 8, 2011.
Cardoso, Jean-Francois, "Blind signal separation: statistical principles", pp. 1-16, (Official Version published as: Proceedings of the IEEE, vol. 9, No. 10, pp. 2009-2025, Oct. 1998).
Hyvarinen et al., "Independent Component Analysis: Algorithms and Applications", Neural Networks Research Centre, Helsinki University of Technology, Finland, Neutral Networks, pp. 1-31, 13(4-5); 411-430, 2000.
Wang et al., "Determining a Number of Objects in an IR Image", U.S. Appl. No. 13/086,006, filed Apr. 28, 2011.
Wang, et al., "Post-Processing a Multi-Spectral Image for Enhanced Object Identification", U.S. Appl. No. 13/324,368, filed Dec. 28, 2011.
Mestha et al., "Removing Environment Factors From Video Signals Captured for Biomedical Measurements", U.S. Appl. No. 13/401,207, filed Feb. 21, 2012.
Pressman et al., "A Transducer for the Continuous External Measurement of Arterial Blood Pressure", External Measurement of Blood Pressure, IEEE Transactions on Bio-Medical Electronics, Apr. 1963, pp. 73-81.
Meigas et al., "Continuous Blood Pressure Monitoring Using Pulse Wave Delay", Proposed Paper; Engineering in Medicine and Biology Society, 2001, vol. 4, pp. 3171-3174, Proceedings of the 23rd Annual Int'l Conf. of the IEEE.
Penaz, J., "Photoelectric Measurement of Blood Pressure, Volume and Flow in the Finger", Dresden, 10th Int. Conf. Med. and Biol. Engineering, 1973, Session 7, N2, Haemodynamics I, pp. 161-164.
Aubert et al., "A Model-Based Study of the Influence of Vaso-Active Drugs on Pulse Delays Measured from the Electrocardiogram", Computers in Cardiology 2007:34:383-386.
Naschitz et al., "Pulse Transit Time By R-Wave-Gated Infrared Photoplethysmography: Review of the Literature and Personal Experience", Journal of Clinical Monitoring and Computing (2004) 18: 333-342, Springer 2005.
Reisner et al., "Utility of the Photoplethysmogram in Circulatory Monitoring", Anesthesiology, vol. 108, No. 5, May 2008, pp. 950-958.
Dalal et al., "Histograms of Oriented Gradients for Human Detection", Proceedings of the Conference on Computer Vision and Pattern Recognition, San Diego, California, USA, pp. 886-893, (2005).
Skaff et al., "Estimating a Visible Vector Representation for Pixels in an Infrared Image", U.S. Appl. No. 13/364,835, filed Feb. 2, 2012.
Xu et al., "Subcutaneous Vein Pattern Detection Via Multi-Spectral IR Imaging in an Identity Verification System", U.S. Appl. No. 13/087,850, filed Apr. 15, 2011.
Mestha et al., "Deriving Arterial Pulse Transit Time From a Source Video Image", U.S. Appl. No. 13/401,286, filed Feb. 21, 2012.
Piratla et al., "Web-Based System and Method for Video Analysis", U.S. Appl. No. 13/417,979, filed Mar. 12, 2012.
Xu et al., "Monitoring Respiration With a Thermal Imaging System", U.S. Appl. No. 13/103,406, filed May 9, 2011.
Wang et al., "Multi-Band Infrared Camera System Optimized for Skin Detection", U.S. Appl. No. 13/416,436, filed Mar. 9, 2012.
Mestha et al., "Processing a Video for Vascular Pattern Detection and Cardiac Function Analysis", U.S. Appl. No. 13/483,992, filed May 30, 2012.
Mestha et al., "A Multi-Filter Array for a Multi-Resolution Multi-Spectral Camera", U.S. Appl. No. 13/239,642, filed Sep. 22, 2011.
Tarvainen et al., "An Advanced De-Trending Method With Application to HRV Analysis", IEEE Trans. Biomed. Eng., vol. 49, No. 2, pp. 172-175, Feb. 2002.
Sahoo et al., "Detection of Atrial Fibrillation from Non- Episodic ECG Data: A Review of Methods", 33rd Annual International Conference of the IEEE EMBS, Boston, Massachusetts USA, (Aug. 30-Sep. 3, 2011).
Kikillus et al., "Three Different Algorithms for Identifying Patients Suffering From Atrial Fibrillation During Atrial Fibrillation Free Phases of the ECG", Computers in Cardiology, 34:801-804, (2007).

\* cited by examiner

DETERMINING CARDIAC ARRHYTHMIA FROM A VIDEO OF A SUBJECT BEING MONITORED FOR CARDIAC FUNCTION

TECHNICAL FIELD

The present invention is directed to systems and methods for processing a time-series signal generated by video images captured of a subject of interest in a non-contact, remote sensing environment such that the existence of a cardiac arrhythmia can be determined for that subject.

BACKGROUND

Monitoring cardiac events is of clinical importance in the early detection of potentially fatal conditions. Current technologies involve contact sensors the individual must wear constantly. Such a requirement can lead to patient discomfort, dependency, loss of dignity, and further may fail due to a variety of reasons including refusal to wear the monitoring device. Elderly cardiac patients are even more likely to suffer from the adverse effects of continued monitoring.

Among many cardiac diseases involving rhythmic disorders, atrial fibrillation (A-fib) represents ⅓ of hospital admissions for cardiac issues. A-fib can cause palpitations, fainting, chest pain, or congestive heart failure and even stroke. It is one of the most common sustained arrhythmias. It increases with age and presents with a wide spectrum of symptoms and severity. There are over 2 million Americans diagnosed with A-fib and is most frequent in elderly patients. Unobtrusive, non-contact, imaging based methods are needed for monitoring cardiac patients for A-fib episodes.

Accordingly, what is needed in this art are sophisticated systems and methods for processing a time-series signal generated by video images captured of a subject of interest in a non-contact, remote sensing environment such that the existence of a cardiac arrhythmia can be determined for that subject.

INCORPORATED REFERENCES

The following U.S. Patents, U.S. Patent Applications, and Publications are incorporated herein in their entirety by reference.

"Subcutaneous Vein Pattern Detection Via Multi-Spectral IR Imaging In An Identity Verification System", U.S. patent application Ser. No. 13/087,850, by Xu et al.

"Deriving Arterial Pulse Transit Time From A Source Video Image", U.S. patent application Ser. No. 13/401,286, by Mestha.

"Processing A Video For Vascular Pattern Detection And Cardiac Function Analysis", U.S. patent application Ser. No. 13/483,992, by Mestha et al.

"Estimating Cardiac Pulse Recovery From Multi-Channel Source Data Via Constrained Source Separation", U.S. patent application Ser. No. 13/247,683, by Mestha et al.

"Systems And Methods For Non-Contact Heart Rate Sensing", U.S. patent application Ser. No. 13/247,575, by Mestha et al.

"Filtering Source Video Data Via Independent Component Selection", U.S. patent application Ser. No. 13/281,975, by Mestha et al.

"Removing Environment Factors From Signals Generated From Video Images Captured For Biomedical Measurements", U.S. patent application Ser. No. 13/401,207, by Mestha et al.

"Detection of Atrial Fibrillation from Non-Episodic ECG Data: A Review Methods", S. K. Sahoo et al., 33$^{rd}$ Annual International Conference of the IEEE EMBS, Boston, Mass. USA, (Aug. 30-Sep. 3, 2011).

"Three Different Algorithms For Identifying Patients Suffering From Atrial Fibrillation During Atrial Fibrillation Free Phases Of The ECG", by N. Kikillus et al, Computers in Cardiology, 34:801-804, (2007).

"Blind Signal Separation: Statistical Principles", Jean-Francois Cardoso, Proceedings of the IEEE, Vol. 9, No. 10, pp. 2009-2025, (October 1998).

"Independent Component Analysis: Algorithms And Applications", Aapo Hyvärinen and Erkki Oja, Neural Networks, 13(4-5), pp. 411-430, (2000).

BRIEF SUMMARY

What is disclosed is a system and method for processing a time-series signal generated by video images captured of a subject of interest in a non-contact, remote sensing environment such that the existence of a cardiac arrhythmia can be determined for that subject. Many A-fib detection algorithms rely on the variability of the RR interval obtained from ECG signals. In the case of A-fib, the chaos and randomness of fluctuations of the stroke volumes lead to large fluctuations of the levels of both the systolic and the diastolic blood pressure. Frequency and duration of A-fib episodes can also change. Since pulse signals from video images correlate with PPG and ECG peaks, the teachings hereof are directed to detecting such episodes by measuring peak-to-peak intervals from the blood volume (also called cardiac volumetric) signals extracted from time-series signals generated from video images of the subject. These peak-to-peak intervals are associated with consecutive heart beats. With an implementation of the teachings hereof, cardiac arrhythmias can be discovered in real-time (or processed offline) from a video captured of the resting cardiac patient. The system and methods disclosed herein provide an effective tool for atrial fibrillation study and cardiac function analysis.

One embodiment of the present method for detecting cardiac arrhythmia from signals generated from video images captured of a subject of interest being monitored for cardiac function in a non-contact remote sensing environment involves the following. First, a time-series signal generated is received. The received time-series signal is generated from video images captured of a region of exposed skin where photoplethysmographic (PPG) signals of a subject of interest can be registered. The video comprise video images captured by at least one imaging channel that is capable of capturing photoplethysmographic signals. The video images can be any combination of: NIR images, RGB images, RGB with NIR images, multispectral images, and hyperspectral video images. Signal separation is performed on the received time-series signals to extract a photoplethysmographic (PPG) signal for the subject. In various embodiments, performing signal separation on the time-series signals comprises performing, using a reference signal, a constrained source separation algorithm on the time-series signals to obtain the PPG signal. The reference signal preferably has a frequency range that approximates a frequency range of the subject's cardiac pulse. Peak-to-peak pulse points are detected in the PPG signal using an adaptive threshold technique with successive thresholds being based on variations detected in previous magnitudes of the pulse peaks. The pulse points are then analyzed to obtain peak-to-peak pulse dynamics. The existence of a cardiac arrhythmia is determined based on the pulse dynamics. In one embodiment, cardiac arrhythmia is determined using a Poincare diagram of the peak-to-peak pulse dynamics. In another embodiment, cardiac arrhythmia is determined based on whether the time interval between consecutive peaks in the processed PPG signal is outside an acceptable limit.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

Figure 1:
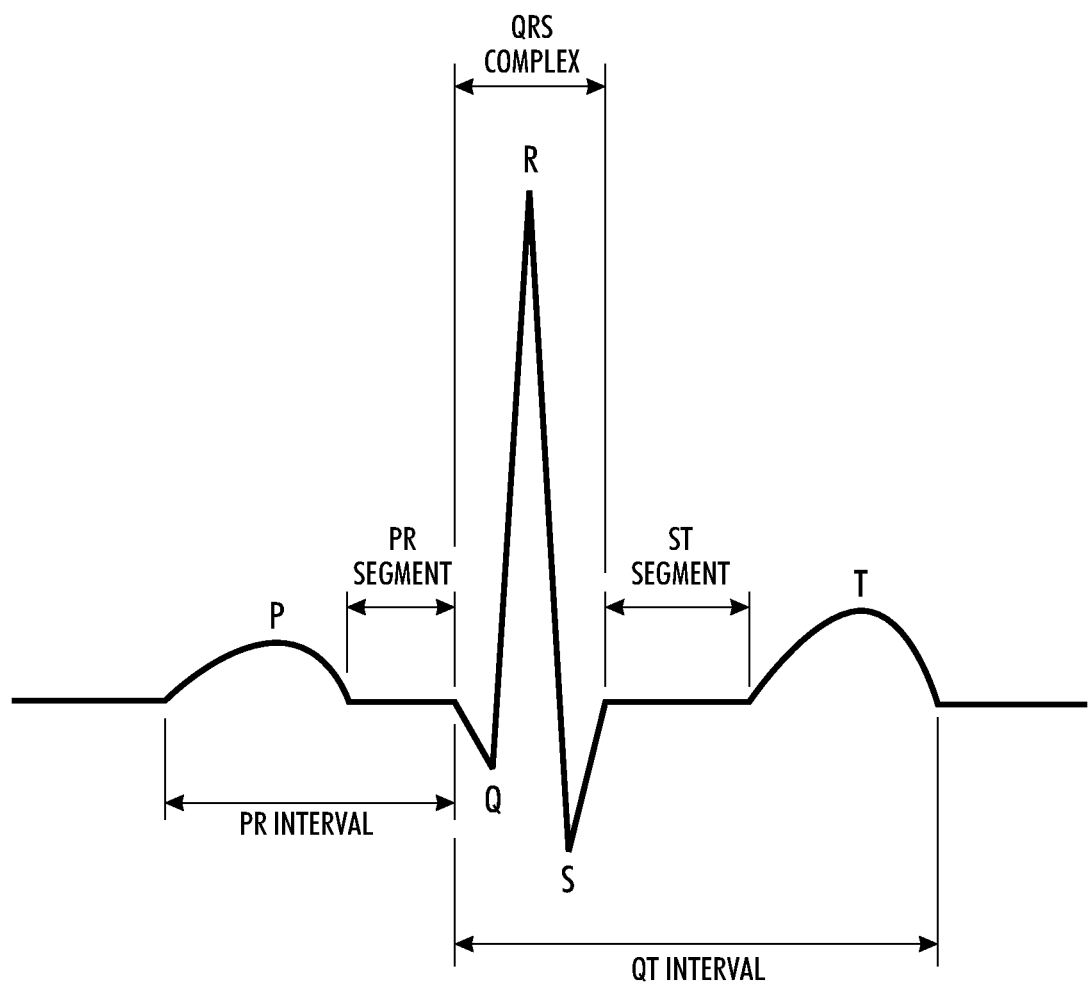
FIG. 1 shows a schematic diagram of normal sinus rhythm for a human heart as seen on an electrocardiogram (ECG)

What is disclosed is a system and method for processing a time-series signal generated by video images captured of a subject of interest in a non-contact, remote sensing environment such that the existence of a cardiac arrhythmia can be determined for that subject.

NON-LIMITING DEFINITIONS

"Cardiac function" refers to the function of the heart and, to a large extent, to the cardio-vascular system. In most species, the heart comprises a muscle which repeatedly contracts to pump hemoglobin through an arterial network. Cardiac function can be impacted by a variety factors including age, stress, disease, overall health, and the like. Cardiac function can also be affected by environmental conditions such as altitude and pressure.

A "subject of interest" refers to a human having a cardiac function. Although the term "human", "person", or "patient" may be used throughout this text, it should be appreciated that the subject may be something other than a human such as, for instance, an animal. Use of "human", "person" or "patient" is not to be viewed as limiting the appended claims strictly to human beings.

A "video" is a sequence of images captured of a subject of interest using a video camera. The video may also contain other components such as, audio, time reference signals, noise, and the like. The video may also be processed to compensate for motion induced blur, imaging blur, or slow illuminant variation. The video may be processed to enhance contrast or brightness. Independent component selection can also be used to emphasize certain content in the video such as, for example, a region containing larger blood vessels. If camera-related noise or environmental factors are adversely affecting extraction of cardiac signals, compensation can be effectuated using the teachings described in the above-incorporated US Patent Application entitled: "Removing Environment Factors From Signals Generated From Video Images Captured For Biomedical Measurements", by Mestha et al. Post-compensated video signals contain decorrelated and noise corrected channels on a per-frame basis.

A "video camera" is a device for acquiring a video. For the purpose of detecting cardiac arrhythmias, as disclosed herein, a near infrared (NIR) camera (4-channel or 1-channel) is preferable. Combinations of visible and IR with multi/hyper-spectral image capture system can also be used. In one embodiment, the video camera comprises a hybrid device capable of capturing both color and infrared images. The video camera may be a multi-spectral or hyperspectral device.

A "video analysis module", in one embodiment, refers to a hardware device with at least one processor executing machine readable program instructions for analyzing video images such that cardiac arrhythmias can be determined in accordance with the teachings hereof. Such a module may comprise, in whole or in part, a software application working alone or in conjunction with one or more hardware resources. Such software applications may be executed by processors on different hardware platforms or emulated in a virtual environment. Aspects of the video analysis module may leverage off-the-shelf software.

"Cardiac arrhythmia", also known as cardiac dysrhythmia, means an irregular heartbeat caused by a change in the heart's electrical conduction system.

"Atrial fibrillation" (AF or A-fib), is one of the most common cardiac arrhythmias. In AF, the normal regular electrical impulses generated by the sinoatrial node are overwhelmed by disorganized electrical impulses usually originating in the roots of the pulmonary veins, leading to irregular conduction of impulses to the ventricles which generate the heartbeat. FIG. 1 shows a schematic diagram of normal sinus rhythm for a human heart as seen on an electrocardiogram (ECG). In atrial fibrillation, the P waves, which represent depolarization of the atria, are absent, with unorganized electrical activity in their place, and irregular R-R intervals due to irregular conduction of impulses to the ventricles. Irregular R-R intervals may be difficult to determine if the rate is extremely rapid. AF increases the risk of stroke; the degree of stroke risk can be up to seven times that of the average population, depending on the presence of additional risk factors such as high blood pressure. It may be identified clinically when taking a pulse measurement. The presence of AF can be confirmed with an ECG (or EKG) which demonstrates the absence of P-waves together with an irregular ventricular rate. AF may occur in episodes lasting from minutes to days ("paroxysmal"), or be permanent in nature. A number of medical conditions increase the risk of AF, particularly narrowing of the mitral valve of the heart (mitral stenosis). Atrial fibrillation may be treated with medications to either slow the heart rate to a normal range ("rate control") or revert the heart rhythm back to normal ("rhythm control"). The evaluation of atrial fibrillation involves diagnosis, determination of the etiology of the arrhythmia, and classification of the arrhythmia.

Figure 2:
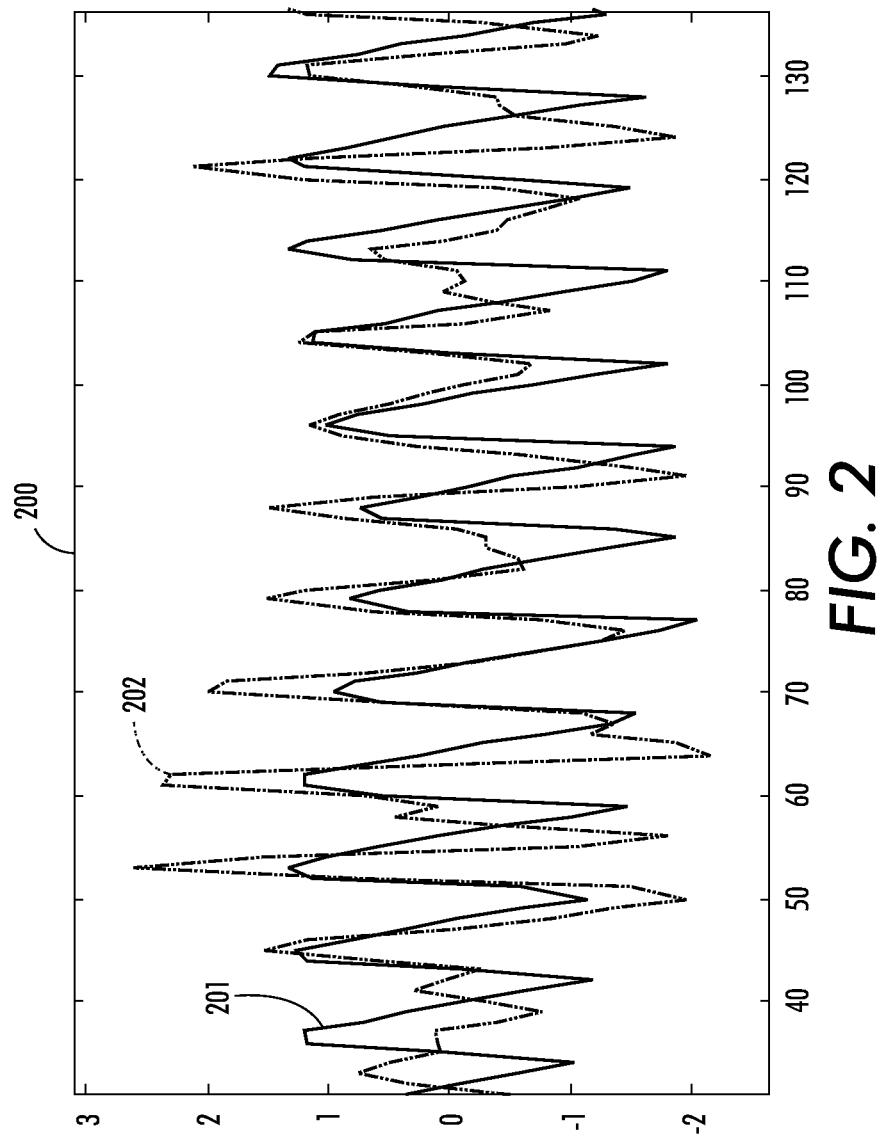
FIG. 2 shows the synchronization between the heart rate signals estimated from the video-based system to a commercial PPG system.

A "photoplethysmographic signal", or simply PPG signal, is a signal which correlates to the subject's cardiac pulse pressure wave. In one embodiment, a region of exposed skin of the subject where such pressure waves can be registered such as, for example, a neck or chest area, is captured by a video camera. The video images are processed to isolate a vascular pattern. The vascular network/pattern is identified in the video images based on, for example, color, spatial features, material identification, and the like. An average of all pixel values in the identified vascular regions within each image frame of the captured video is computed to obtain a channel average on a per-frame basis. A global channel average is computed, for each channel, by adding the channel averages across multiple image frames and dividing by the total number of frames. The channel average is subtracted from the global channel average and the result divided by a global channel standard deviation to obtain a zero-mean unit variance time-series signal for each of the isolated vascular regions. The obtained time-series signal are normalized and filtered to remove undesirable frequencies. The resulting time-series signals for the vascular regions contain the sum total of volumetric pressure changes within those regions. Arterial pulsations comprise a dominant component of these time-series signals. These time-series signals are processed using an independent component analysis technique to extract PPG signals. FIG. 2 shows a plot 200 of a cardiac signal 201 obtained from a heart rate estimation algorithm as disclosed in the above-incorporated reference entitled: "Estimating Cardiac Pulse Recovery From Multi-Channel Source Data Via Constrained Source Separation", by Mestha et al., and a PPG signal 202 obtained via a MP36 Biopac System with a sensor attached to an earlobe of the subject. Clearly, peak occurrence coincides with signals obtained from the PPG system meaning that when the ventricles contract volumetric blood signature of pulsating blood can be seen in the heart rate signal obtained from having processed the video. The present method is based on reflectance-mode photoplethysmography, in which the returned light from the skin contains the heart beat signal. The light from the source enters into deeper structures of the skin and blood vessels. Although there is some increase in light due to reflected light from more erythrocytes when blood volume increases, this directly increased light is negligible when compared to the absorbed light returning from the deeper tissues. Thus, the negative signal peaks in heart rate signals of FIG. 2 correspond to increased blood volume which occurs during ventricular contraction. The signals recorded contain blood volume changes obtained from all blood vessels (e.g., arteries, arterioles, capillaries, venules, and veins) when compared only to electrical signals obtained using an ECG. These signals are then processed in a manner more fully disclosed herein.

Example Video Capture Device

Figure 3:
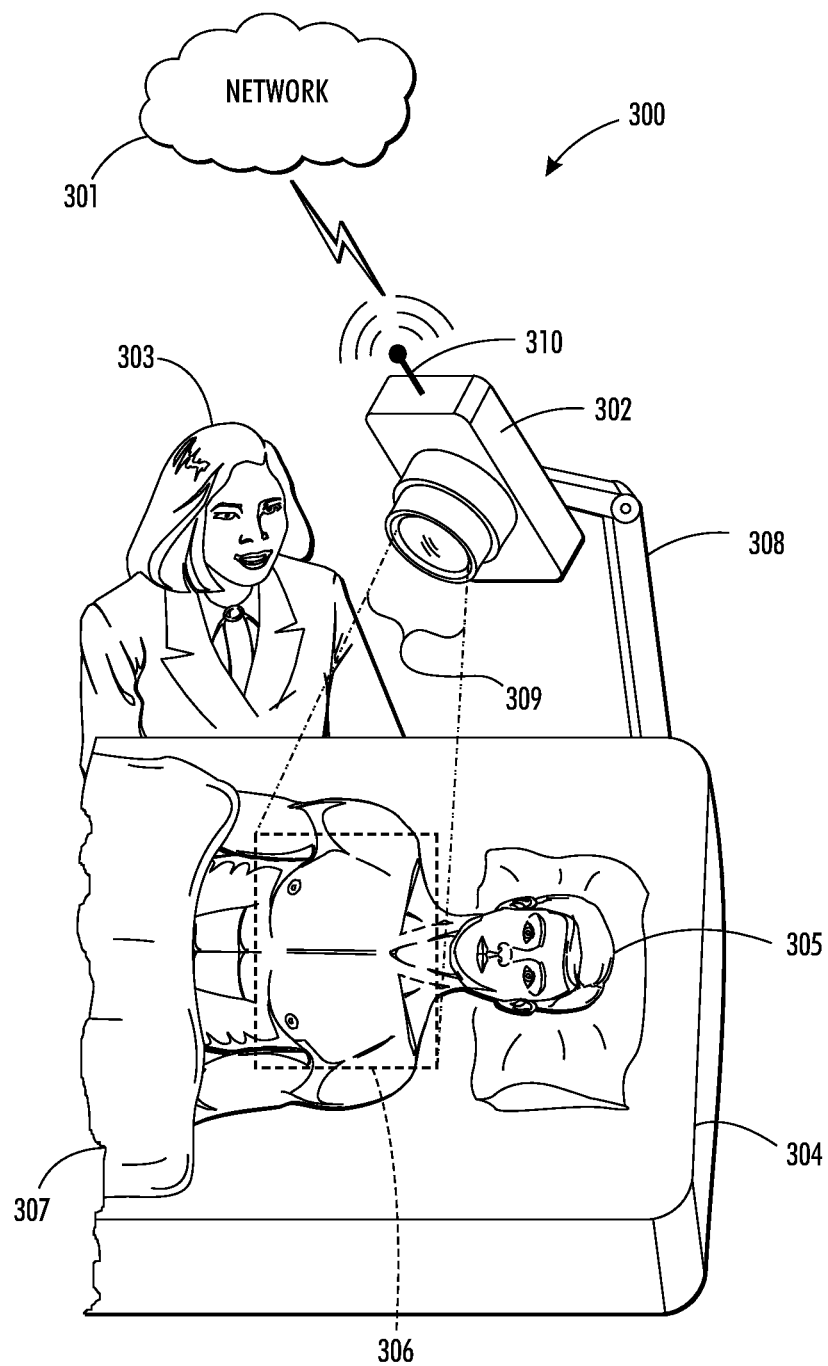
FIG. 3 illustrates one embodiment of an example video camera system for acquiring a video signal of a subject of interest being monitored for cardiac function.

Reference is now being made to FIG. 3 which illustrates one embodiment of an example video camera system for acquiring a video signal of a subject of interest being monitored for cardiac function in accordance with the teachings hereof.

Examination room 300 has an example video capture system 302 being operated by technician or nurse 303 standing at the bedside 304 of subject of interest 305 shown resting his/her head on a pillow while his/her body is partially covered by sheet 307. Camera system 302 is rotatably fixed to support arm 308 such that the camera's field of view 309 can be directed by nurse 303 onto an area of exposed skin of a chest area 306 of patient 305 for continuous monitoring of cardiac function. Support arm 308 is on a set of wheels so that the image capture system can be moved from bed to bed and room to room. Although patient 305 is shown in a prone position lying in a bed, it should be appreciated that images of the subject of interest being monitored for cardiac function can be captured while the subject is positioned in other supporting devices such as, for example, a chair or wheelchair, standing up, including walking or moving. Camera system 302 captures video images of the subject of interest to be monitored for cardiac function. The captured video images comprise multi-channel source data such as RGB and/or multi-spectral acquired over time. Camera 302 comprises imaging sensors which may be a single sensor or a sensor array including a plurality of individual or separate sensor units. A central processor integral to camera 302 and in communication with a memory (not shown) functions to detect changes in the status of sensors and outputting an alarm, notice, report, and the like, if a change in any hardware or software of the camera has been detected. Other sensors are capable of sensing a change of status of patient 305 and issue an alarm or notification via transmission element 310 to a nurse, doctor, or technician in the event that the monitored cardiac function of the patient falls outside a set of predefined parameters.

Antenna 310 is used to communicate the video images to various remote devices. Transmitter 310 may be a wired (e.g., Ethernet) connection utilizing an Ethernet network consisting of Ethernet cables and an Ethernet hub that is in communication with a network 301. Camera system 302 may include both wireless and wired elements and may be connected via other means such as coaxial cable, radio frequency, Bluetooth, or any other manner for communicating data. Network 301 receives the transmitted video signals and wirelessly communicates the received video images to various devices such as, for instance, a workstation with a display device, for processing. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communications pathway. Techniques for placing devices in networked communication are well established. As such, a further discussion as to specific networking techniques has been omitted. Any of the networked devices may include a network interface card or network communication system.

Flow Diagram of One Example Embodiment

Figure 4:
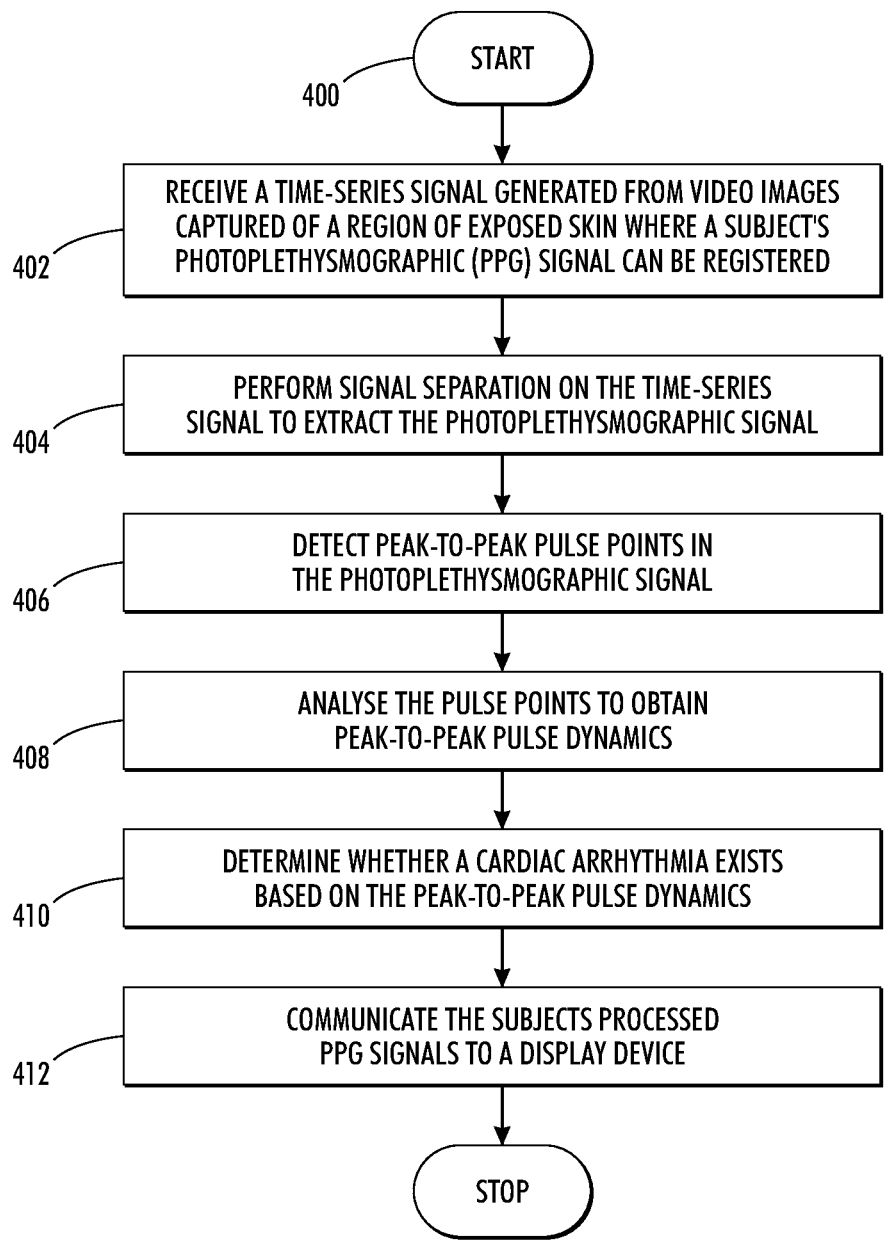
FIG. 4 is a flow diagram which illustrates one embodiment of the present method for detecting cardiac arrhythmia from signals generated from video images captured of the subject of interest of FIG. 3.

Reference is now being made to the flow diagram of FIG. 4 which illustrates one example embodiment of the present method for detecting cardiac arrhythmia from signals generated from video images captured of a subject of interest being monitored for cardiac function. Flow processing begins at step 400 and immediately proceeds to step 402.

At step 402, receive a time-series signal generated from video images captured of a region of exposed skin where photoplethysmographic signals of a subject of interest can be registered. The video comprises video images captured by at least one imaging channel capable of capturing the subject's photoplethysmographic signals. The time-series signal may be retrieved from a storage device for processing or obtained from a remote device over a network.

At step 404, perform signal separation on the time-series signals to extract an estimated photoplethysmographic signal for the subject. Blind Source Separation recovers unobserved signals from a mixed set of observed signals without any prior information being known about how the signals were mixed. Typically, the observed signals are acquired as output from sensors where each sensor receives or otherwise detects a different combination of source signals. One form of blind source separation is independent component analysis (ICA). ICA is a decomposition technique for uncovering independent source signal components from a set of observations that are composed of linear mixtures of underlying sources, i.e., independent components of the observed data. Constrained source separation is an independent component analysis method for separating time-series signals into additive subcomponents using a reference signal as a constraint. In one embodiment, the reference signal has a frequency range that approximates a frequency range of the subject's cardiac pulse. Not all constraints can be used for constrained independent component analysis (cICA) because some constraints infringe classical ICA equivariant properties. Constraints that define or restrict the properties of the independent components should not infringe the independence criteria. Additional conditions can be incorporated using, for example, sparse decomposition of signals or fourth-order cumulants into the contrast function, to help locate the global optimum separating the components.

Figure 5:
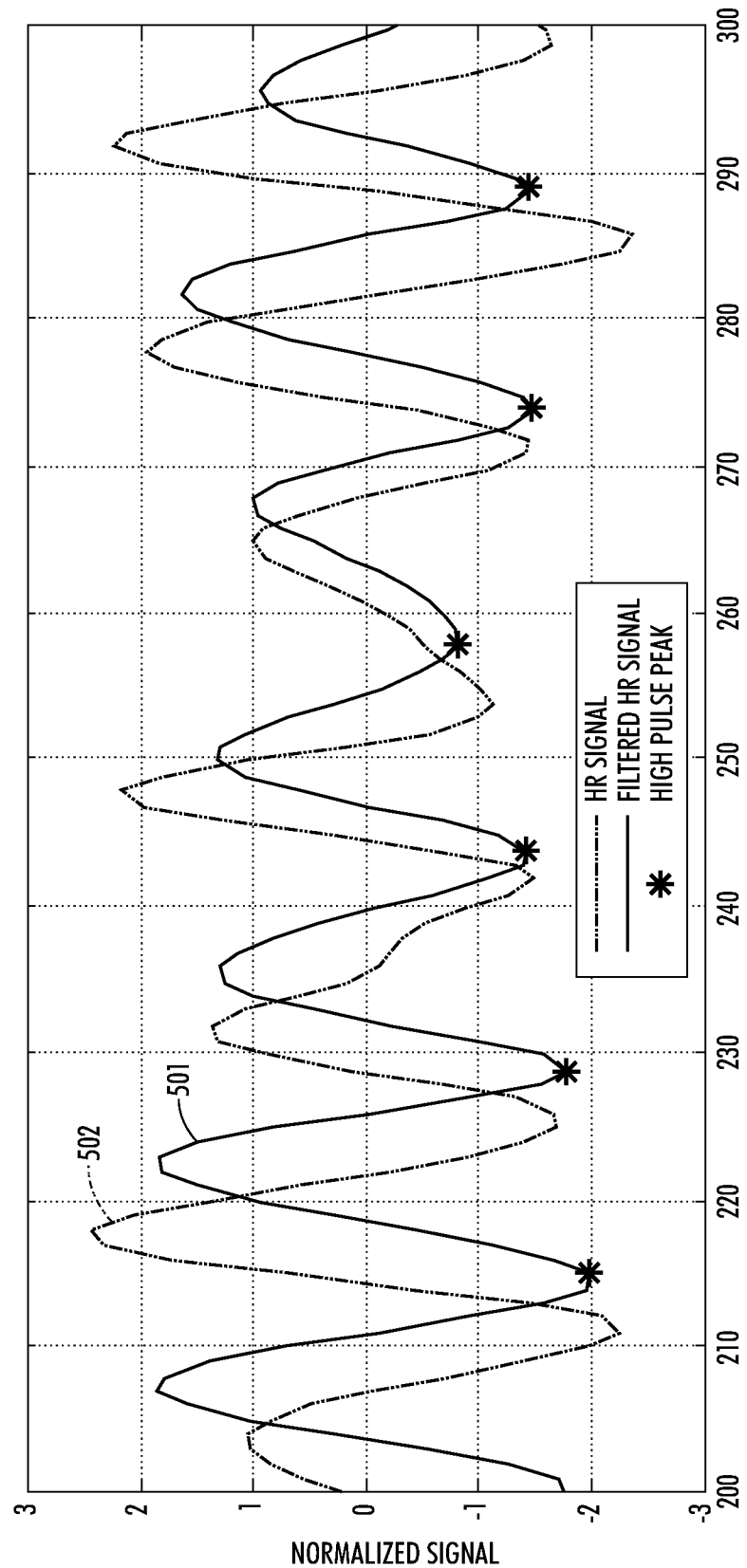
FIG. 5 shows a normalized (unfiltered) heart rate signal and a normalized (filtered) heart rate signal filtered using a moving average filter with a 40 frame delay.
Figure 6A:
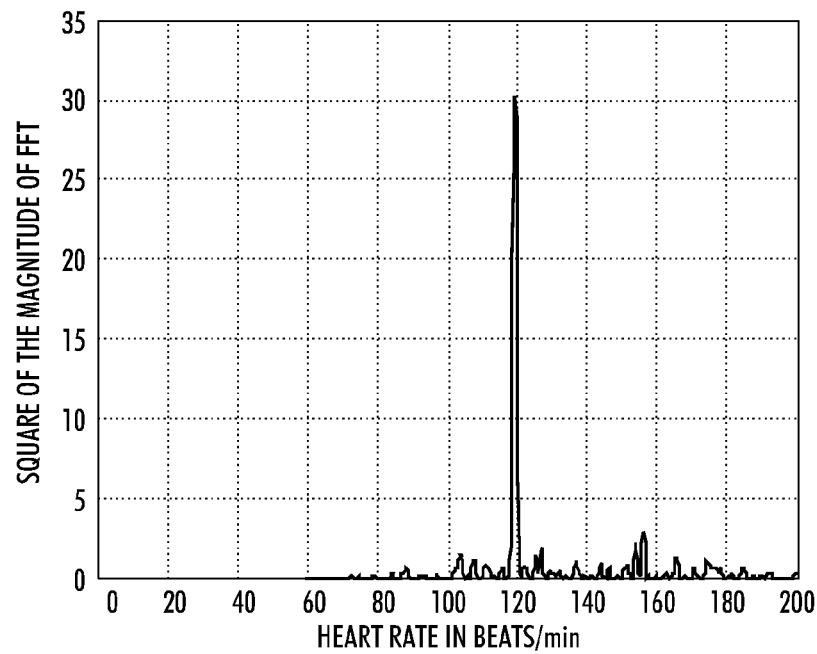
FIGS. 6A-B show the power spectral densities of the unfiltered and filtered heart rate signals of FIG. 5, respectively.
Figure 6B:
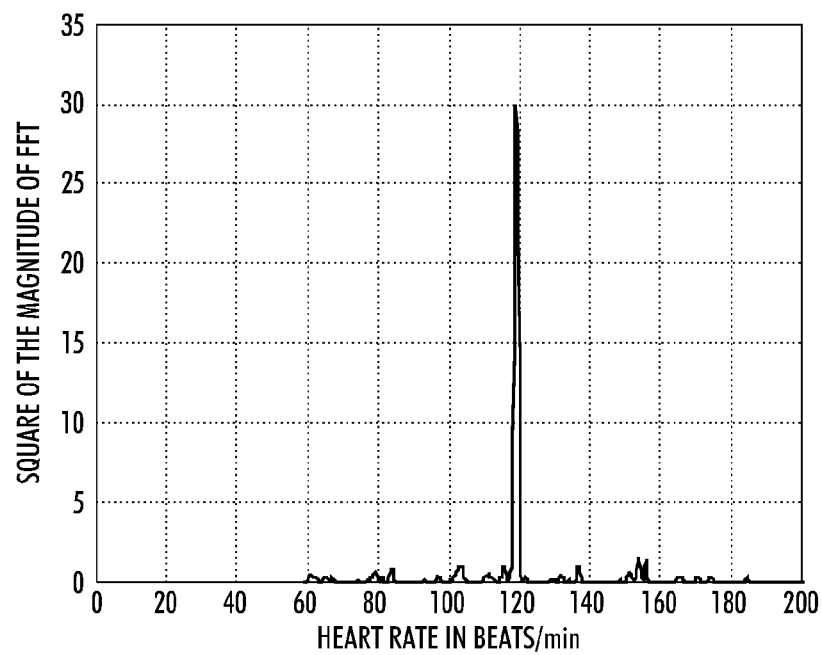

The obtained PPG (heart rate) signal is converted to zero-mean unit variance. To remove sub-bands in the heart rate signal, a filtering step is performed in order to improve peak detection accuracy. HR signals can be filtered using, for example, a moving average filter with a suitable moving window of size N frames. One example moving average filter is given as:

$$y(n) = \frac{1}{N}\sum_{1}^{N} x(n-i) \quad (1)$$

where N is the number of frames in the moving window, x is the unfiltered photoplethysmographic signal, y is the filtered photoplethysmographic signal, n is the current frame i is the index designating the moving frame. The moving average filter can also provide corrections to missing peaks. Additional corrections may be necessary based on estimating the average of the amplitudes obtained from previous peaks. FIG. 5 shows a normalized unfiltered heart rate signal 501 and a normalized heart rate signal 502 filtered with a moving average filter with a 40 frame delay. Peak points are obtained with a threshold of 0.15. The plot of FIG. 5 was obtained from infant videos from a neonatal intensive care unit (ICU). FIG. 6 A&B shows the respective power spectral densities of the unfiltered and filtered heart rate signals of FIG. 5. A small phase distortion generated from the moving average filter due to the moving window size does not add significant detrimental effects on the A-fib detection accuracy. Ectopic heart beats, irregular beats arising with decrease in blood supply to the heart, can give a longer peak to peak (PP) interval. They can either be removed from the HR signal or replaced with interpolated values (or with values determined to be more acceptable).

At step 406, detect peak-to-peak pulse points in the photoplethysmographic signal. Peak-to peak intervals are relatively easy to detect. Since these peaks coincide with the PPG signal, the count of the number of peaks per minute provide an estimate of the heart rate. To identify arrhythmia prior to on-set, statistics about peak-to-peak dynamics are obtained such as, for example, the time interval between two consecutive heart beats using, for instance, a Poincare diagram of peak-to-peak dynamics to identify A-fib; and excess time taken by the present PP interval. A threshold detector is used to determine the peak pulse point. The threshold can be made adaptive in order to avoid false (or missing) pulse peaks if a single threshold is too high. One adaptation strategy involves determining a next threshold based on the variations detected in the previous magnitudes of pulse peaks. The pulse peaks of FIG. 5 were identified using a peak-to-peak detection algorithm with a fixed threshold. In other embodiments, peak detection is guided by an estimated heart rate. To increase the accuracy of peak-to-peak interval, the time-series signal can also be pre-upsampled to a standard sampling frequency such as, for instance, 256 Hz.

Figure 7:
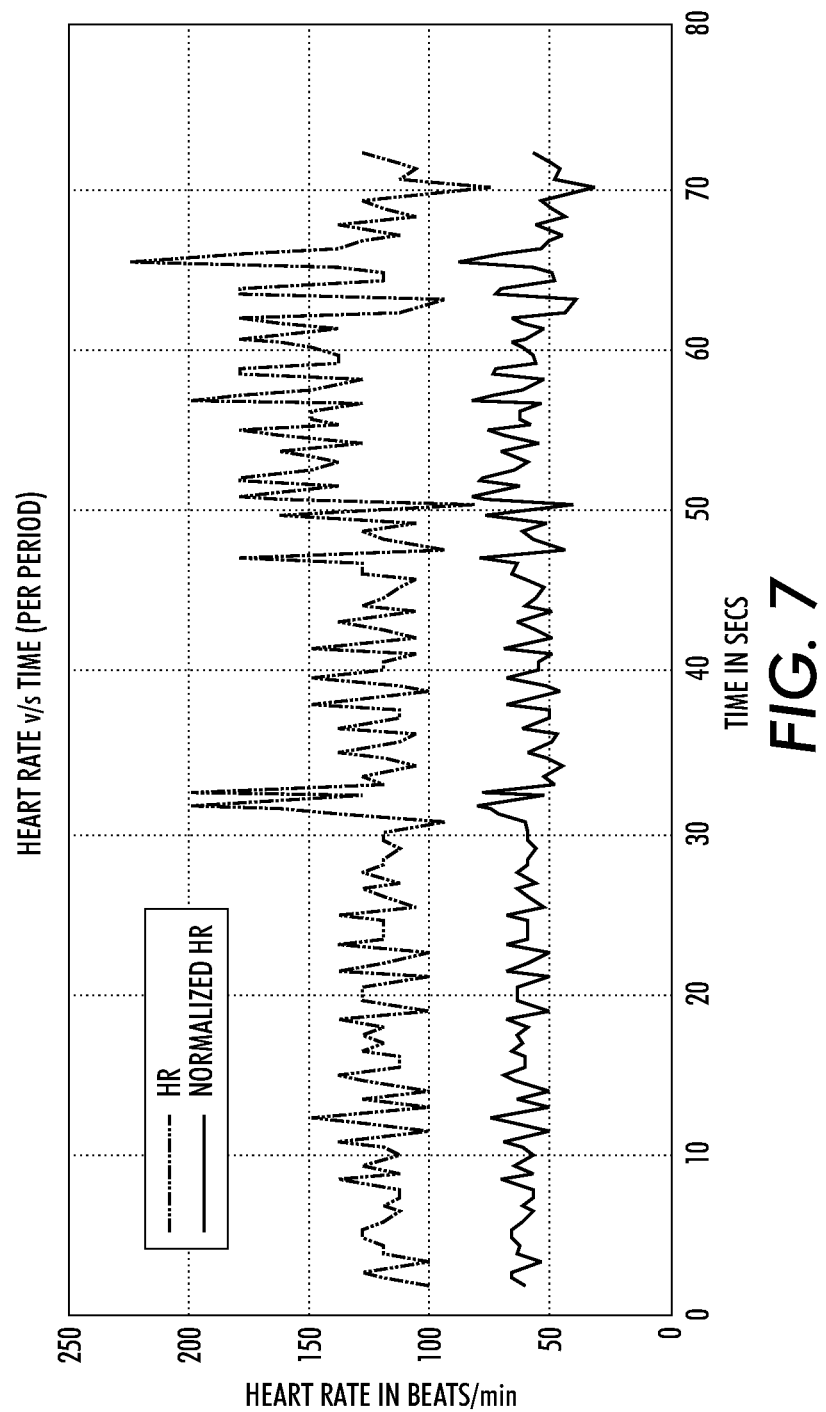
FIG. 7 shows heart rate with respect time when calculated using the inverse of the PP(n) and $PP_{normalized}(n)$ intervals.

Peak-to-peak intervals are preferably normalized to 60 beats per minute using Eq. (2) in order to make it independent from pulse variations. This also helps in those embodiments wherein it is desirable to compare peak-to-peak intervals across different patients. In one embodiment, the peak-to-peak intervals are normalized by:

$$PP_{normalized}(n) = PP(n) \times \frac{\text{heart rate}_{15sec}}{60} \quad (2)$$

where, PP(n) is the PP interval for the $n^{th}$ cardiac cycle, heart rate$_{15sec}$ is the mean heart rate of the previous 15 seconds, and $PP_{normalized}(n)$ is the normalized PP interval for $n^{th}$ cardiac cycle. FIG. 7 shows the time evolution of the heart rate with respect to time for approximately one minute when calculated by inverting the PP intervals. Clearly, the normalized signal has low pulse variations.

Figure 8A:
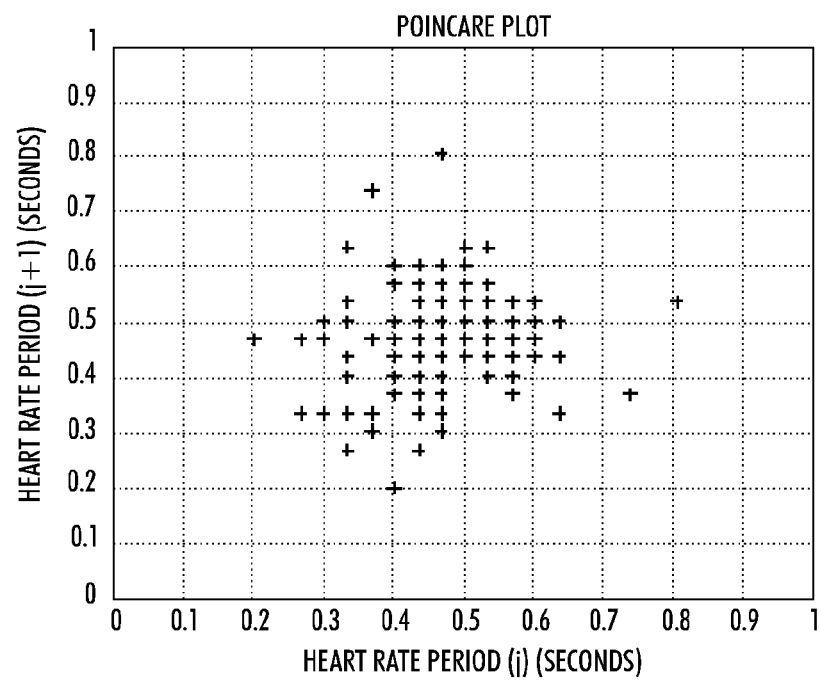
FIG. 8A shows the Poincare plot PP(n) intervals (i.e., without normalization)
Figure 8B:
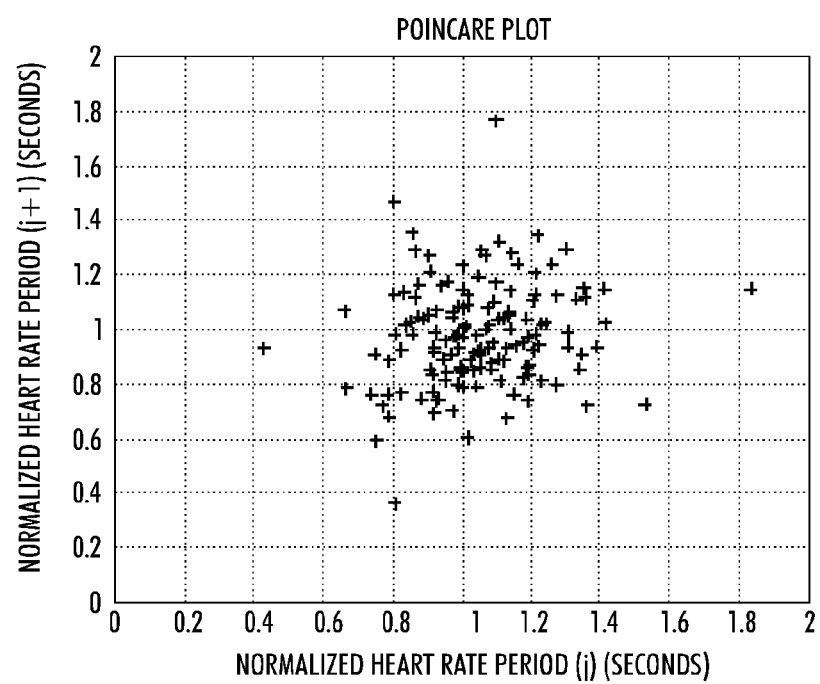
FIG. 8B shows the Poincare plot $PP_{normalized}(n)$ intervals (i.e., with normalization)

At step 408, analyze the pulse points to obtain peak-to-peak pulse dynamics. FIGS. 8A-B, show the Poincare plots between PP interval of the current cardiac cycle ($PP_n$) to the PP interval of the next cardiac cycle ($PP_{n+1}$). FIG. 8A shows the Poincare plot of PP(n) intervals (without normalization). FIG. 8B shows the Poincare plot $PP_{normalized}(n)$ intervals (with normalization). These results were obtained from a video of an infant in a Neonatal ICU. The Poincare plot of a person with a normal sinus rhythm obtained using ECG-based system will be close to a straight line with a slope of 45 degree. For an example of Poincare plot for normal sinus rhythm, the reader is respectfully directed "*Detection of Atrial Fibrillation from Non-Episodic ECG Data: A Review Methods*", by S. K. Sahoo et al., $33^{rd}$ Annual International Conference of the IEEE EMBS, Boston, Mass. USA, (Aug. 30-Sep. 3, 2011), and for patients with A-fib to: "*Three Different Algorithms For Identifying Patients Suffering From Atrial Fibrillation During Atrial Fibrillation Free Phases Of The ECG*", by N. Kikillus et al, Computers in Cardiology, 34:801-804, (2007). Poincare plots from patients with A-fib look very different (not along the 45 degree line). Contours contain various sizes (e.g., circles, triangles, etc.), distributed without much structure. Poincare plots can also be drawn by rotating with respect to x-axis (not shown).

At step 410, determine whether a cardiac arrhythmia exists based upon the pulse dynamics. A-fib is not usually detected unless specifically looked for. To identify A-fib in patients, various parameters can be extracted from the Poincare plot such as, for instance, centroid, vertical deviation, horizontal deviation, ratio of vertical and horizontal standard deviation, ellipse area, correlation coefficient, regression coefficient, and the equation of the regression line. Other statistics can be obtained to identify A-fib. Such statistics are discussed in the above-cited reference: "*Three Different Algorithms For Identifying Patients Suffering From Atrial Fibrillation During Atrial Fibrillation Free Phases Of The ECG*". Statistical data obtained across A-fib patients can be compared to those with normal sinus rhythms to identify the presence of A-fib. A visual inspection of the Poincare plot captured over a prolonged duration (at about 1 hour of PP intervals) on A-fib patients can be sufficient to show an indication of A-fib. Additional risk levels can be assigned based on where the points lie on the Poincare plot. Chronic A-fib is usually preceded by paroxysmal atrial fibrillation (PAT), a premature atrial contraction which triggers a flurry of atrial activity. In some systems, further tuning of the A-fib detection algorithm may be required to estimate the on-set of PAT. Atrial Flutter may also be detected using a high speed IR camera system.

At step 412, communicate the subject's processed PPG signal to a display device. In this particular embodiment, further processing stops. In another embodiment, an alarm is initiated which indicates that the subject's heart arrhythmia is not within acceptable parameters. Initiating an alarm can be, for example, activating a light, making an audible noise, or otherwise generating a signal which activates a device which, in turn, performs an action or provides a notification. The kind of alarm signal being generated will depend on the particular embodiment wherein the teachings hereof are implemented. In this particular embodiment, once the alarm signal is activated, further processing stops. In another embodiment, processing repeats such that the subject's cardiac function is continuously monitored. The present system can be used in conjunction with other health monitoring equipment or integrated therewith such that the initiated alarm signal causes these other device to perform intended functions.

It should be appreciated that the flow diagrams hereof are illustrative. One or more of the operative steps illustrated in any of the flow diagrams may be performed in a differing order. Other operations, for example, may be added, modified, enhanced, condensed, integrated, or consolidated with the steps thereof. Such variations are intended to fall within the scope of the appended claims. All or portions of the flow diagrams may be implemented partially or fully in hardware in conjunction with machine executable instructions.

Example Functional Block Diagram

Figure 9:
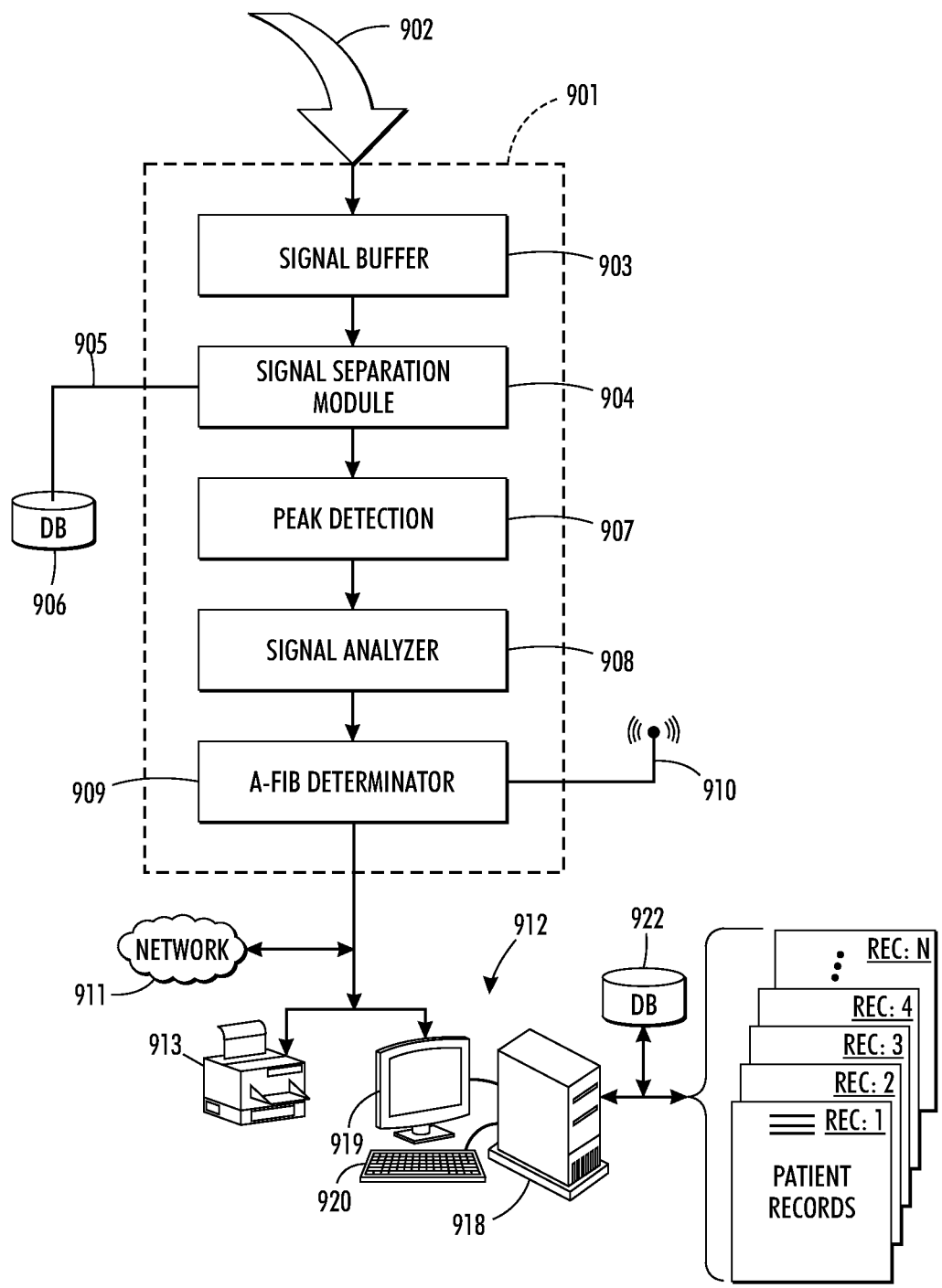
FIG. 9 illustrates a block diagram of one example processing system 900 capable of implementing various aspects of the present method described with respect to the flow diagram of FIG. 4.

Reference is now being made to FIG. 9 which illustrates a block diagram of one example processing system 900 capable of implementing various aspects of the present method described with respect to the flow diagram of FIG. 4.

The embodiment of FIG. 9, signal processing system 901 receives a time-series signal 902 generated from video images into buffer 903. The received time-series signals have been captured of a region of exposed skin where photoplethysmographic signals of a subject of interest can be registered. Buffer 903 may be used for queuing information about the received signals (or images) such as, for instance, one or more target regions within the image frames, size of the video, time/date information, and the like. The buffer may be configured to also store data, mathematical formulas and other representations to facilitate processing of the image in accordance with the teachings hereof. Signal separation module 904 obtains the buffered signal and performs signal separation on the received time-series signal 902 to extract the estimated photoplethysmographic signal 905 and stores the extracted signal to storage device 906. Peak detection module 907 receives photoplethysmographic signal 905 from signal separation module 904, or alternatively from storage device 908, and detects peak-to-peak pulse points in the photoplethysmographic signal, as described with respect to the flow diagram of FIG. 4, and outputs pulse points. Signal analyzer 908 analyzes the pulse points to obtain peak-to-peak pulse dynamics. A-Fib Determinator 909 determines the existence of a cardiac arrhythmia based upon the pulse dynamics. These results are also displayed on display device 919 in real-time or processed offline. In this embodiment, if the subject's cardiac arrhythmia parameters are not within predetermined levels set by, for example, the subject's cardiac specialist, then a notification signal is sent using, for example, transmission element 910, which may assume any of a wide variety of communication elements depending on the design of the system wherein the teachings hereof find their intended uses. In another embodiment, cardiac arrhythmia is determined based on whether the time interval between consecutive peaks in the processed PPG signal is outside an acceptable limit. Notification may further involve initiating an audible sound which provides an indication to the user hereof or specialist that the subject's cardiac arrhythmias require attention. Such a notification may take the form of a canned audio message or, for instance, a bell tone or a sonic alert being activated, or initiating a visible light which provides an indication such as, for instance, a blinking colored light. The communicated notification message can be a text, audio, and/or video message. Such embodiments are intended to be encompassed within the scope of the appended claims.

Any of the cardiac signals and parameters determined by signal processing unit 901 are communicated to workstation 912 and multi-function print system device 913 for further processing or rendering to hardcopy. The subject's cardiac data may further be communicated to remote devices over network 911. Many aspects of network 911 are commonly known and a further discussion as to the construction and/or operation of a specific network configuration has been omitted. Suffice it to say, data is transmitted in packets between networked devices via a plurality of communication devices and links using established protocols. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communications pathway. Computer workstation 912 is shown comprising a computer case 918 housing a motherboard, CPU, memory, interface, storage device, and a communications link such as a network card. The computer workstation is also shown having a display device 919 such as a CRT, LCD, or touchscreen display. An alphanumeric keyboard 920 and a mouse (not shown) effectuate a user input. In the embodiment of FIG. 9, computer system 911 implements database 922 wherein various records are stored, manipulated, and retrieved in response to a query. Although the database is shown as an external device, the database may be internal to computer case 918 mounted on a hard disk housed therein. A record refers to any data structure capable of containing information which can be indexed, stored, searched, and retrieved in response to a query. Patient information can be stored and/or retrieved to any of the records in database 922. It should be appreciated that the workstation has an operating system and other specialized software configured to display a variety of numeric values, text, scroll bars, pull-down menus with user selectable options, and the like, for entering, selecting, or modifying information displayed on the display device.

Any of the modules and processing units of FIG. 9 are in communication with workstation 912 via pathways (not shown) and may further be in communication with one or more remote devices over network 911. It should be appreciated that some or all of the functionality for any of the modules of system 901 may be performed, in whole or in part, by components internal to workstation 912 or by a special purpose computer system. It should also be appreciated that various modules may designate one or more components which may, in turn, comprise software and/or hardware designed to perform the intended function. A plurality of modules may collectively perform a single function. Each module may have a specialized processor and memory capable of retrieving and executing machine readable program instructions. A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through network 911.

It will be appreciated that the above-disclosed and other features and functions, or alternatives thereof, may be desirably combined into many other different systems or applications. Various presently unforeseen or unanticipated alternatives, modifications, variations, or improvements therein may become apparent and/or subsequently made by those skilled in the art which are also intended to be encompassed by the following claims. Accordingly, the embodiments set forth above are considered to be illustrative and not limiting. Various changes to the above-described embodiments may be made without departing from the spirit and scope of the invention. The teachings hereof can be implemented in hardware or software using any known or later developed systems, structures, devices, and/or software by those skilled in the applicable art without undue experimentation from the functional description provided herein with a general knowledge of the relevant arts. Moreover, the methods hereof can be implemented as a routine embedded on a personal computer or as a resource residing on a server or workstation, such as a routine embedded in a plug-in, a driver, or the like. Furthermore, the teachings hereof may be partially or fully implemented in software using object or object-oriented software development environments that provide portable source code that can be used on a variety of computer, workstation, server, network, or other hardware platforms. One or more of the capabilities hereof can be emulated in a virtual environment as provided by an operating system, specialized programs or leverage off-the-shelf computer graphics software such as that in Windows, Java, or from a server or hardware accelerator or other image processing devices.

One or more aspects of the methods described herein are intended to be incorporated in an article of manufacture, including one or more computer program products, having computer usable or machine readable media. The article of manufacture may be included on at least one storage device readable by a machine architecture embodying executable program instructions capable of performing the methodology described herein. The article of manufacture may be included as part of an operating system, a plug-in, or may be shipped, sold, leased, or otherwise provided separately either alone or as part of an add-on, update, upgrade, or product suite. It will be appreciated that various of the above-disclosed and other features and functions, or alternatives thereof, may be combined into other systems or applications. Various presently unforeseen or unanticipated alternatives, modifications, variations, or improvements therein may become apparent and/or subsequently made by those skilled in the art which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for detecting cardiac arrhythmia from signals generated from video images captured of a subject of interest being monitored for cardiac function in a non-contact remote sensing environment, the method comprising:
receiving a time-series signal generated from video images captured of a region of exposed skin where a photoplethysmographic (PPG) signal of a subject of interest can be registered, said video comprising video images captured by at least one imaging channel capturing PPG signals;
processing said time-series signal to extract a PPG signal for said subject;
filtering said PPG signal to obtain a filtered PPG signal, said filtering comprising:

$$y(n) = \frac{1}{N} \sum_{1}^{N} x(n-i)$$

where N is a number of frames in a moving window, x is said unfiltered PPG signal, n is a current frame and i is an index designating said moving window frame;
detecting peak-to-peak pulse points in said filtered PPG signal;
analyzing said pulse points to obtain peak-to-peak pulse dynamics; and
determining whether a cardiac arrhythmia exists based on said pulse dynamics.

2. The method of claim 1, wherein said video images comprise any combination of: NIR images, RGB images, RGB with NIR images, multispectral images, and hyperspectral video images.

3. The method of claim 1, wherein, in advance of obtaining said time-series signal, pre-processing said video to compensate for any of: a motion induced blur, an imaging blur, and slow illuminant variation.

4. The method of claim 1, wherein performing signal separation on said time-series signal comprises performing, using a reference signal, a constrained source separation algorithm on said time-series signal to obtain said PPG signal.

5. The method of claim 1, wherein said peak-to-peak pulse points are detected in said filtered PPG signal using an adaptive threshold technique with successive thresholds being based on variations detected in previous magnitudes of said pulse peaks.

6. The method of claim 1, further comprising pre-processing said time-series signal by upsampling said signal to a standard sampling frequency in order to enhance the accuracy of detecting said peak-to-peak pulse points.

7. The method of claim 1, wherein said cardiac arrhythmia is determined using a Poincare diagram of said peak-to-peak pulse dynamics, said Poincare diagram showing a relationship between consecutive beats.

8. The method of claim 1, further comprising normalizing said detected peak-to-peak pulse points to a frequency of 60 bpm to reduce pulse variations in said filtered PPG signal.

9. The method of claim 1, wherein determining said cardiac arrhythmia comprises determining whether a time interval between consecutive peaks in said filtered PPG signal is outside an acceptable limit for said subject.

10. The method of claim 1, wherein said time-series signal comprises one of: stored values, and values generated from a streaming video.

11. The method of claim 1, further comprising comparing said subject's peak-to-peak pulse dynamics across different patients.

12. The method of claim 1, further comprising communicating said subject's peak-to-peak pulse dynamics to a display device.

13. A system for detecting cardiac arrhythmia from signals generated from video images captured of a subject of interest being monitored for cardiac function in a non-contact remote sensing environment, the system comprising:

a display device; and a processor in communication with a memory, said processor executing machine readable instructions for performing:

receiving a time-series signal generated from video images captured of a region of exposed skin where a photoplethysmographic (PPG) signal of a subject of interest can be registered, said video comprising video images captured by at least one imaging channel capturing PPG signals;

processing said time-series signal to extract a PPG signal for said subject;

filtering said PPG signal to obtain a filtered PPG signal, said filtering comprising:

$$y(n) = \frac{1}{N}\sum_{1}^{N} x(n-i)$$

where N is a number of frames in a moving window, x is said unfiltered PPG signal, n is a current frame and i is an index designating said moving window frame;

detecting peak-to-peak pulse points in said filtered PPG signal;

analyzing said pulse points to obtain peak-to-peak pulse dynamics;

determining whether a cardiac arrhythmia exists based on said pulse dynamics; and communicating said pulse dynamics to said display device.

14. The system of claim 13, wherein said video images comprise any combination of: NIR images, RGB images, RGB with NIR images, multispectral images, and hyperspectral video images.

15. The system of claim 13, wherein, in advance of obtaining said time-series signal, pre-processing said video to compensate for any of: a motion induced blur, an imaging blur, and slow illuminant variation.

16. The system of claim 13, wherein performing signal separation on said time-series signal comprises performing, using a reference signal, a constrained source separation algorithm on said time-series signal to obtain said PPG signal.

17. The system of claim 13, wherein said peak-to-peak pulse points are detected in said filtered PPG signal using an adaptive threshold technique with successive thresholds being based on variations detected in previous magnitudes of said pulse peaks.

18. The system of claim 13, further comprising pre-processing said time-series signal by upsampling said signal to a standard sampling frequency in order to enhance the accuracy of detecting said peak-to-peak pulse points.

19. The system of claim 13, wherein said cardiac arrhythmia is determined using a Poincare diagram of said peak-to-peak pulse dynamics, said Poincare diagram showing a relationship between consecutive beats.

20. The system of claim 13, further comprising normalizing said detected peak-to-peak pulse points to a frequency of 60 bpm to reduce pulse variations in said filtered PPG signal.

21. The system of claim 13, wherein determining said cardiac arrhythmia comprises determining whether a time interval between consecutive peaks in said filtered PPG signal is outside an acceptable limit for said subject.

\* \* \* \* \*